(12) United States Patent
Clawson et al.

(10) Patent No.: US 7,842,007 B2
(45) Date of Patent: Nov. 30, 2010

(54) APPARATUS AND METHODS FOR ISOLATING HUMAN BODY AREAS FOR LOCALIZED COOLING

(76) Inventors: Burrell E. Clawson, 883 W. 16th St., Newport Beach, CA (US) 92663; Richard A. Weiss, 421 San Bernardino, Newport Beach, CA (US) 92663

( * ) Notice: Subject to any disclaimer, the term of this patent is extended or adjusted under 35 U.S.C. 154(b) by 914 days.

(21) Appl. No.: 11/587,866

(22) PCT Filed: Apr. 29, 2005

(86) PCT No.: PCT/US2005/014848
§ 371 (c)(1),
(2), (4) Date: Oct. 26, 2006

(87) PCT Pub. No.: WO2005/107834
PCT Pub. Date: Nov. 17, 2005

(65) Prior Publication Data
US 2007/0250140 A1     Oct. 25, 2007

Related U.S. Application Data

(60) Provisional application No. 60/567,272, filed on Apr. 30, 2004.

(51) Int. Cl.
*A61M 5/00* (2006.01)
(52) U.S. Cl. ...................................... 604/112; 604/113

(58) Field of Classification Search .................. 604/112, 604/113, 93.01, 500, 512, 304–308, 179, 604/180, 291, 23, 26, 1; 607/104, 96, 108–111; 128/849; 600/555, 362, 575; 606/22; 239/53
See application file for complete search history.

(56) References Cited

U.S. PATENT DOCUMENTS

| 683,075 A | 9/1901 | Schneider ..................... 433/90 |
| 1,500,107 A | 7/1924 | Chandler ..................... 433/80 |
| 1,660,096 A | 2/1928 | Schiele ....................... 128/622 |
| 2,127,094 A | 8/1938 | Strauss |
| 2,187,560 A | 1/1940 | Reilly .......................... 128/62 |

(Continued)

FOREIGN PATENT DOCUMENTS

EP         0156080         10/1985

(Continued)

*Primary Examiner*—Nicholas D Lucchesi
*Assistant Examiner*—Weng Lee
(74) *Attorney, Agent, or Firm*—Stout, Uxa, Buyan & Mullins; Frank J. Uxa

(57) ABSTRACT

Apparatus (8) and methods are provided for facilitating medical procedures, such as providing injections to human or animal patients. The apparatus and methods mitigate against discomfort and/or pain often experienced by a patient receiving an injection for a therapeutic or a cosmetic purpose. The apparatus and methods are effective to isolate a surface area of a human or animal body, even an irregularly shaped surface area of a body, for enabling localized preparation of the skin, for example for localized cooling of the skin.

19 Claims, 2 Drawing Sheets

U.S. PATENT DOCUMENTS

| | | | |
|---|---|---|---|
| 2,349,607 A | 5/1944 | Berger | 433/80 |
| 2,452,903 A | 11/1948 | Coffey | 32/17 |
| 2,754,590 A | 7/1956 | Cohen | 433/90 |
| 3,018,778 A | 1/1962 | Brilliant | |
| 3,029,809 A | 4/1962 | Madlung | 128/62 |
| 3,078,856 A | 2/1963 | Bender et al. | 132/321 |
| 3,109,192 A | 11/1963 | Levenson | 128/62 |
| 3,228,398 A | 1/1966 | Leonard et al. | 604/1 |
| 3,242,519 A | 3/1966 | Murray | 128/62 |
| 3,267,512 A | 8/1966 | Wiley | 15/561 |
| 3,401,690 A | 9/1968 | Martin | 128/62 |
| 3,565,075 A | 2/1971 | Jerry | 604/307 |
| 3,660,323 A | 5/1972 | Raguse | 128/62 |
| 3,876,314 A | 4/1975 | Nehring | 604/2 |
| 3,964,482 A | 6/1976 | Gerstel et al. | 604/896 |
| 3,972,995 A | 8/1976 | Tsuk et al. | 128/156 |
| 3,975,570 A | 8/1976 | Ono et al. | 128/156 |
| 3,987,202 A | 10/1976 | Okun | 424/70 |
| 4,147,831 A | 4/1979 | Balinth | 128/156 |
| 4,161,176 A | 7/1979 | Harris, II et al. | 128/155 |
| 4,194,290 A | 3/1980 | Vallhonrat | 433/141 |
| 4,201,211 A | 5/1980 | Chandrasekaran et al. | 604/897 |
| 4,206,843 A | 6/1980 | Rainey | 206/216 |
| 4,218,155 A | 8/1980 | Weidner | 401/132 |
| 4,224,898 A | 9/1980 | Flagg et al. | 119/1 |
| 4,286,592 A | 9/1981 | Chandrasekaran et al. | 604/890 |
| 4,307,717 A | 12/1981 | Hymes et al. | 128/156 |
| 4,310,509 A | 1/1982 | Berglund et al. | 604/307 |
| 4,325,367 A | 4/1982 | Tapper | 128/207.21 |
| 4,367,732 A | 1/1983 | Poulsen et al. | 604/307 |
| 4,397,395 A | 8/1983 | McKelvey | 211/60 |
| 4,401,130 A | 8/1983 | Halford et al. | 604/1 |
| 4,448,307 A | 5/1984 | Roggenkamp | 206/369 |
| 4,466,973 A | 8/1984 | Rennie | 424/267 |
| 4,472,141 A | 9/1984 | Dragan | 433/90 |
| 4,486,193 A | 12/1984 | Shaw et al. | 604/890 |
| 4,541,472 A | 9/1985 | Eriksson et al. | 164/504 |
| 4,556,055 A | 12/1985 | Bonner, Jr. | 128/82.1 |
| 4,561,435 A | 12/1985 | McKnight et al. | 604/304 |
| 4,566,055 A | 1/1986 | Klees et al. | 362/162 |
| 4,566,280 A | 1/1986 | Burr | 60/757 |
| 4,569,355 A | 2/1986 | Bitterly | 128/691 |
| 4,599,372 A | 7/1986 | Bardoliwalla et al. | 523/336 |
| 4,600,593 A | 7/1986 | Swisher | 426/438 |
| 4,614,191 A | 9/1986 | Perler | 128/399 |
| 4,620,528 A | 11/1986 | Arraval | 128/62 |
| 4,621,594 A | 11/1986 | Kubis | 123/41.09 |
| 4,624,656 A * | 11/1986 | Clark et al. | 604/23 |
| 4,626,455 A | 12/1986 | Karabedian | 428/35 |
| 4,628,564 A | 12/1986 | Youssef | 15/167 |
| 4,655,768 A | 4/1987 | Marecki et al. | 424/448 |
| 4,661,476 A | 4/1987 | Lane et al. | 514/60 |
| 4,664,291 A | 5/1987 | Gunderson | 221/309 |
| 4,690,156 A | 9/1987 | Kikuchi et al. | 128/804 |
| 4,699,792 A | 10/1987 | Nick et al. | 604/307 |
| 4,710,191 A | 12/1987 | Kwiatek et al. | 604/304 |
| 4,728,323 A | 3/1988 | Matson | 604/304 |
| 4,745,916 A | 5/1988 | Seber | 128/155 |
| 4,747,739 A | 5/1988 | Bowman et al. | 411/368 |
| 4,748,022 A | 5/1988 | Busciglio | 424/195 |
| 4,756,310 A | 7/1988 | Bitterly | 128/400 |
| 4,758,217 A * | 7/1988 | Gueret | 604/500 |
| 4,767,398 A | 8/1988 | Blasius, Jr. | |
| 4,795,421 A | 1/1989 | Blasius, Jr. et al. | 604/1 |
| 4,804,177 A | 2/1989 | Rosson | 272/71 |
| 4,809,946 A | 3/1989 | Morrison | 249/197 |
| 4,854,319 A | 8/1989 | Tobin | 128/380 |
| 4,869,250 A | 9/1989 | Bitterly | 128/400 |
| 4,887,994 A | 12/1989 | Bedford | 604/1 |
| 4,895,727 A | 1/1990 | Allen | 424/642 |
| 4,976,906 A | 12/1990 | Nakasone et al. | 264/139 |
| 4,978,510 A | 12/1990 | Smith | 422/310 |
| 4,988,341 A | 1/1991 | Columbus et al. | 604/304 |
| 4,989,730 A | 2/1991 | Lemoine | 206/362 |
| 4,990,144 A | 2/1991 | Blott | 604/304 |
| 5,016,651 A | 5/1991 | Stalcup et al. | 128/898 |
| 5,027,829 A | 7/1991 | Larsen | 128/804 |
| 5,097,846 A | 3/1992 | Larsen | 128/804 |
| 5,112,297 A | 5/1992 | Stalcup et al. | 604/1 |
| 5,117,812 A | 6/1992 | McWhorter | 128/24 R |
| 5,120,325 A | 6/1992 | Dow, Jr. | 604/304 |
| 5,122,056 A | 6/1992 | Barbee | 433/80 |
| 5,130,005 A | 7/1992 | Hurwitt et al. | 204/192.12 |
| 5,136,792 A | 8/1992 | Janecke | 34/78 |
| 5,137,230 A | 8/1992 | Coffinberry | 244/118.5 |
| 5,140,908 A | 8/1992 | Sullivan, Jr. | 102/322 |
| 5,148,966 A | 9/1992 | Minase et al. | 288/149 |
| 5,156,911 A | 10/1992 | Stewart | 428/355 |
| 5,191,761 A | 3/1993 | Janeke | 60/224 |
| 5,209,921 A | 5/1993 | Brobyn et al. | 425/45 |
| 5,214,820 A | 6/1993 | Shumway et al. | 15/118 |
| 5,214,821 A | 6/1993 | Burrow et al. | |
| 5,254,120 A | 10/1993 | Cinberg et al. | 606/109 |
| 5,260,327 A | 11/1993 | Kim et al. | 514/405 |
| 5,279,047 A | 1/1994 | Janecke | 34/78 |
| 5,286,320 A | 2/1994 | McGrath et al. | 156/83 |
| 5,295,952 A | 3/1994 | Pietrafitta | 604/1 |
| 5,297,390 A | 3/1994 | Sood | 60/740 |
| 5,300,018 A | 4/1994 | Walsh et al. | 604/1 |
| 5,300,103 A * | 4/1994 | Stempel et al. | 607/108 |
| 5,314,423 A | 5/1994 | Seney | 606/20 |
| 5,321,947 A | 6/1994 | Sood et al. | 60/737 |
| 5,338,495 A | 8/1994 | Steiner et al. | 261/28 |
| 5,344,418 A | 9/1994 | Ghaffari | 606/9 |
| 5,358,480 A | 10/1994 | Melcher et al. | 604/1 |
| 5,368,860 A | 11/1994 | Sunami et al. | 424/448 |
| 5,378,226 A | 1/1995 | Hanifi et al. | 604/3 |
| 5,384,048 A | 1/1995 | Hazen et al. | 210/605 |
| 5,385,677 A | 1/1995 | Venable | 210/748 |
| 5,387,450 A | 2/1995 | Stewart | 428/40 |
| 5,397,564 A | 3/1995 | Seki et al. | 424/45 |
| 5,399,313 A | 3/1995 | Ross et al. | 420/448 |
| 5,403,162 A | 4/1995 | Chen | 416/246 |
| 5,409,590 A | 4/1995 | Hurwitt et al. | 204/298.2 |
| 5,417,901 A | 5/1995 | Hartman et al. | 264/45.5 |
| 5,433,950 A | 7/1995 | Popp | 424/400 |
| 5,447,930 A | 9/1995 | Nayak | 514/239 |
| 5,486,172 A | 1/1996 | Chess | 606/20 |
| 5,511,563 A | 4/1996 | Diamond | 128/848 |
| 5,520,925 A | 5/1996 | Maser | 424/443 |
| 5,567,375 A | 10/1996 | Filion et al. | 264/251 |
| 5,572,745 A | 11/1996 | Mainus | 2/171.2 |
| 5,581,805 A | 12/1996 | Rennick | 2/2 |
| 5,630,811 A | 5/1997 | Miller | 606/9 |
| 5,663,460 A | 9/1997 | Yamamoto et al. | 568/829 |
| 5,704,906 A | 1/1998 | Fox | 604/1 |
| 5,714,020 A | 2/1998 | Perrin | 148/581 |
| 5,715,559 A | 2/1998 | Mitri | |
| 5,762,494 A | 6/1998 | Archambault | |
| 5,829,976 A | 11/1998 | Green | 433/89 |
| 5,878,459 A | 3/1999 | McParland | 15/114 |
| 5,921,963 A * | 7/1999 | Erez et al. | 604/192 |
| 5,934,006 A | 8/1999 | Stevenson et al. | 43/42.06 |
| 5,976,550 A | 11/1999 | Engel et al. | 424/195.1 |
| 5,989,567 A | 11/1999 | Dolisi | 424/400 |
| 6,119,296 A | 9/2000 | Noe et al. | |
| 6,125,847 A | 10/2000 | Lin | 128/204.17 |
| 6,231,835 B1 * | 5/2001 | Kimura | 424/45 |
| 6,235,265 B1 | 5/2001 | Logsdon | 424/45 |
| 6,258,044 B1 | 7/2001 | Lonky et al. | |
| 6,297,044 B1 | 10/2001 | Eisen et al. | |
| 6,325,769 B1 | 12/2001 | Klopotek | 601/2 |

| | | | |
|---|---|---|---|
| 6,333,356 B1 | 12/2001 | Ptchelintsev et al. | 514/631 |
| 6,413,255 B1 | 7/2002 | Stern | 606/41 |
| 6,423,038 B1 | 7/2002 | Vancaillie | 604/279 |
| 6,547,467 B2 | 4/2003 | Quintero | 401/132 |
| 6,623,440 B1 | 9/2003 | Weldon | 604/1 |
| 6,902,554 B2 * | 6/2005 | Huttner | 604/500 |
| 2005/0182364 A1 * | 8/2005 | Burchman | 604/112 |

FOREIGN PATENT DOCUMENTS

| | | |
|---|---|---|
| EP | 0331392 | 9/1989 |
| EP | 0393727 | 10/1990 |
| WO | WO 89/11872 | 12/1989 |

* cited by examiner

APPARATUS AND METHODS FOR ISOLATING HUMAN BODY AREAS FOR LOCALIZED COOLING

RELATED APPLICATION

This application claims the benefit of U.S. provisional application No. 60/567,272 filed on Apr. 30, 2004, the entire disclosure of which is incorporated herein by this reference.

BACKGROUND

The present invention is generally directed to apparatus and methods for facilitating medical procedures, such as providing injections to humans and animals, and is more specifically directed to apparatus and methods effective to facilitate or to prepare a body area for one or more injections, for example by isolating an area of a body for localized cooling.

Injecting materials, for example, antibiotics, medications and cosmetic materials, into a human body is a very common and effective way of treating various conditions in a human. Such injections can cause a substantial amount of discomfort and/or pain. In some people, even the relatively small amount of discomfort or pain caused by injections can result in avoidance of needed injections. Discomfort and pain can be alleviated by applying topical anesthetics to the injection site. However, such topical anesthetics often require a substantial amount of time before they become effective once they are placed on an area of a body.

More effective apparatus and methods are needed for reducing occurrence of discomfort, pain and/or fear of a person undergoing a medical procedure such as receiving an injection.

SUMMARY OF THE INVENTION

The present invention provides apparatus and methods for isolating an area of a human body, for example, such an area which is to be injected with a beneficial substance, to allow localized application of a topical anesthetic or other skin preparation agent. The localized application of a topical anesthetic provides anesthetic effect to the desired target area without detrimentally affecting body surfaces outside the localized area.

In an especially advantageous embodiment of the invention, the topical skin preparation agent is a coolant, for example a vapocoolant, to allow localized and preferably rapid cooling of the area to provide an anesthetic-like effect. When the present apparatus is used prior to or during an otherwise painful or uncomfortable procedure on a body area, the remainder of the body is advantageously substantially unaffected by the skin preparation agent, for example, is substantially unaffected by cooling of the area. Moreover, once the procedure, for example, injection, has been completed, normal sensitivity at the injected area preferably returns relatively quickly so that the human is subjected to no detrimental long term effects of the cooling. In one aspect, the present invention provides for a rapid cooling of a well defined area of the body, for example a well defined surface area of the body, which, after such area is anesthetized, for example, cooled, and injected, returns to normal sensitivity with substantially no side effects.

In a specific embodiment, injection site isolation apparatus for isolating an area of a human body for localized cooling are provided. The apparatus may comprise a member comprising a first layer and a second layer, for example, a first absorbent layer and a second layer, advantageously a relatively less absorbent second layer.

The first layer preferably includes an absorbent first material, and has a first surface, a substantially opposing second surface and a first through aperture extending between the first and second surfaces. The first layer is preferably absorbent to the skin preparation agent, for example, an evaporative coolant, or vapocoolant, to be passed through the first through aperture. The first through aperture is sized to allow an evaporative coolant, for example, halogen-containing organic compounds, such as fluoro carbons, fluoro/chloro carbons, ethyl chloride and the like and mixtures thereof, to pass toward and/or into and/or through the aperture and come into contact with an area of a human body when the first surface of the first layer is placed in proximity to the area of the human body.

The second layer includes a second material which is less absorbent than the first material and has a second through aperture. The second through aperture preferably is at least as large as, for example is larger than, the first through aperture. In a preferred embodiment, the second through aperture substantially overlaps, or substantially entirely encompasses the first through aperture. The second layer is secured to the first layer, for example by heat bonding, the use of one or more adhesive and the like and combinations thereof, and is disposed in proximity to the second surface of the first layer. For example, the first and second layers are advantageously located in a layered relationship such that the second surface of the first layer substantially abuts the second layer.

In one very useful embodiment, the member is sized and configured to be held in and manipulated by a single adult human hand, for example, a hand of a physician or other caretaker.

The member may be configured so that the first surface of the first layer, that is, the surface of the member which comes in contact with an area of a human body to be treated, is convex when the member is at rest, for example, when substantially no external force is being applied to the member other than gravity. The member may further be configured so that the second layer has a surface, for example an outer surface which faces away from the first surface of the first layer, which is concave when the member is at rest. Advantageously, the member preferably is sufficiently flexible so that when applied to a surface of a body to be treated, even one or more irregularly shaped areas of the body, the member can be substantially conformed to the surface.

In one embodiment of the invention, the first material is a porous material, such as a porous polymeric material, for example a porous or foamed polyolefin, e.g., polyethylene, material. Other suitable materials, for example, other suitable polymeric materials, may also be used in or as the first material. The first material should be such as to be effective in the present invention without causing any significant adverse reaction or interference with the human undergoing treatment, or with the skin preparation agent being used, or with the treatment to be administered to the human.

The first through aperture often has a size and shape effective to allow cooling of an intended area of a human body. For example, the first through aperture may have a size and shape effective to allow preparation, e.g., cooling, of only or substantially only the intended area of a human or animal body. Often, the first through aperture is substantially centrally located in the first layer, although the aperture may be located in other non-centrally located regions of the first layer. The first through aperture may have a circular shape, an oval shape, a polygonal shape, an elongated, for example narrow linear shape, or irregular shape, or any other shape suitable for the intended application. For example, in some embodiments, the first through aperture has an elongated shape having a size or length substantially corresponding to a size or length of a crease in human skin that is to be injected with collagen or other cosmetically beneficial material.

In one very useful embodiment, the second material included in the second layer is a substantially solid material, for example, a substantially solid polymeric material, for example a substantially solid polyolefin, for example, polyethylene, material. Other suitable materials, for example, other suitable polymeric materials may also be used in or as the second material.

In one embodiment, the second material is relatively harder than the first material. The second material may be more rigid than the first material. Even in this situation, however, it is preferred that the member be sufficiently flexible or deformable so as to be able to be manually manipulated, for example, so as to be able to conform the apparatus to irregularly-shaped areas of the body. For example, the second layer may be made of a non-absorbent deformable material.

Advantageously, the second layer is structured to facilitate placing the first layer in contact with one or more irregularly-shaped areas of a human body. For example, the second layer preferably is effective to facilitate applying increased force or pressure on the first layer to cause the first surface of the first layer to conform to an irregularly shaped human body part.

The second through aperture located in the second layer, preferably substantially overlaps, or substantially entirely overlaps, or for example, substantially encompasses, the first through aperture. In an especially advantageous embodiment of the invention, the second through aperture has a cross-sectional area of at least about two times or at least about three times or more the cross-sectional area of the first through aperture.

Preferably, the second through aperture is shaped to enhance contact between the body surface and the first layer. For example, the second through aperture has a configuration, for example, a shape and/or size and/or thickness, that facilitates applying increased force or pressure on the first layer to cause the first layer to conform to one or more irregularly shaped areas of the human body, for example, relative to a reference second through aperture defining a circular shape (having a circular cross-section) and having the same cross-sectional area as the second through aperture.

In a very useful embodiment, the second layer includes one or more fingers or projections extending into the second through aperture. Such fingers or projections facilitate applying increased force or pressure on the first layer to cause the first layer to more closely conform to the surface of the body, relative to an otherwise identical device without such fingers of projections.

The present apparatus may be made using conventional manufacturing techniques, for example, conventional polymeric material processing techniques used for producing polymeric material composites. For example, the first layer and second layer may be made separately and then secured together, or may be made together and secured in such manufacturing processing. The two layers may be made and sized separately, the through apertures are then formed in the layers, and the layers having the apertures therethrough are then secured together. The first layer may be secured to the second layer using conventional techniques, such as one or more of heat processing, adhesives, multi-material molding, co-molding, ultrasound processing, other polymeric material composite manufacturing techniques, and combinations thereof. Preferably, the layers are secured together using heat bonding without the use of adhesives or the like.

In one embodiment, the second layer includes one or more ribs near the periphery of the second layer opposite the first layer. Such ribs are structured to be effective to inhibit dripping of skin preparation material, for example, condensed evaporative coolant, from the member. Further, the second layer may include at least one opening, for example a plurality of openings near the periphery of the second layer, for example inside of the one or more ribs. The openings are sized and positioned to capture excess skin preparation material, for example, to capture liquid evaporant coolant and substantially prevent leakage or dripping thereof from the member. Upon entering the openings in the second layer, such excess material becomes absorbed by the absorbent first layer, thereby reducing the chance that the excess material will contact the skin.

The present apparatus provides for a focused application of a skin preparation agent, such as an evaporative coolant, to achieve the desired degree of localized, focused preparation, e.g., cooling, of a desired area of a body to be treated, for example, an area of a body to be injected. In addition, the present apparatus is advantageously structured to reduce or prevent any leakage, dripping or spillage caused by the skin preparation agent, for example caused by condensation of the skin preparation agent, e.g., evaporative coolant, from the member.

The present invention further provides methods of treating a localized intended area of a human or animal body. In a broad aspect of the invention, a method is provided which generally comprises the step of providing a member including an absorbent first layer having a first surface, a substantially opposing second surface, and a first through aperture extending between the first and second surfaces, and a relatively less absorbent second layer having a second through aperture substantially encompassing the first through aperture. Preferably, the member comprises an apparatus of the invention as described and shown elsewhere herein.

The method further comprises the step of placing the member in contact with a human or animal body so that the first layer is in contact with the body and the first through aperture substantially circumscribes an intended area of the body to be treated, and preparing the intended area for treatment by passing a skin preparation agent or material, for example, an evaporative coolant, through the first and second through apertures while the member is so placed. The skin preparation material is passed through the through apertures by spraying, brushing or otherwise applying the skin preparation material to the intended area. The skin preparation material typically is in a fluid, e.g., gas or liquid or vaporous, form during the application thereof, but it is to be appreciated that materials in gel form or solid form may also be used in accordance with the present invention.

In one embodiment, the method further comprises the step of treating the intended area that has been prepared, for example, injecting a therapeutically or cosmetically beneficial material into the area.

In a more specific embodiment, the step of preparing comprises anesthetizing the intended area, for example, cooling the intended area by application of a skin preparation agent comprising a vapocoolant.

The step of treating may be performed while the apparatus is in contact with the body. For example, after application of a vapocoolant to the intended area, the area may be injected with a therapeutically or cosmetically beneficial material by inserting a distal end of a needle through the first and second through apertures and into the intended area.

Alternatively, the member may be removed from the body prior to the step of treating.

In one aspect, the invention provides a method for preparing an area of a human body for one or more injections is provided. The method generally comprises placing an apparatus in accordance with the present invention on an intended area of a human body to receive an injection. A skin preparation agent, preferably an evaporative coolant, is passed toward, into and/or through the first through aperture while the apparatus is so placed. This results in localized preparation, preferably cooling, of the intended area of the human body, for example, to effectively anesthetize the intended area without substantially anesthetizing surface areas surrounding the intended area. The apparatus may be removed from the body prior to administering one or more injections to the intended area of the body.

Any and all features described herein and combinations of such features are included within the scope of the present invention provided that the features of any such combination are not mutually inconsistent.

These and other aspects and advantages of the present invention are apparent in the following detailed description and claims, particularly when considered in conjunction with the following drawings in which like parts are identified by like reference numerals.

DETAILED DESCRIPTION OF THE DRAWINGS

Figure 1:
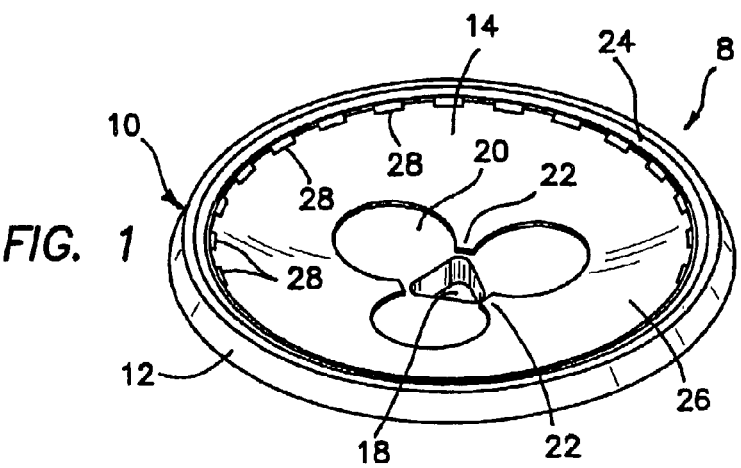
FIG. 1 is a perspective view of a coolant spray shield member in accordance with the present invention.

Referring now to the Figures, an apparatus in accordance with the present invention is shown generally at 8. Apparatus 8 is useful for isolating a specific, intended area of a body, for example to prepare the intended area for receiving an injection or other medical procedure that may be uncomfortable or painful. In the embodiment shown, apparatus 8 comprises a substantially dome-shaped member 10 including a first layer 12 and an abutting second layer 14. When in use, the first layer 12 is placed in contact with the body area to be treated.

The first layer 12 includes a first surface 12a and a substantially opposing second surface 12b. First layer 12 is preferably made of an absorbent material, such as a porous polymeric material, for example, but not limited to, a porous polyethylene. The size and/or shape of the first layer 12 are selected to be effective to cover, for example shield, a suitably sized area of the body circumscribing the intended area to be treated. For example, the first layer is sized and shaped to facilitate placing at least a portion of the layer 12, and in particular at least a portion of a first surface 12a of the layer 12, in contact with an area of a human body in proximity to, for example in contact with, the area of the human body to be injected.

By way of example, and without limitation, the layer 12 may have a diameter in a range of about 2 inches or less, to about 3 inches, or about 4 inches or more, and a thickness in the range of about 0.2 inch or less, to about 0.5 inch, or about 0.6 inch or more. A very useful embodiment provides that the layer 12 has a diameter of about 2.0 inches or about 3.0 to about 3.5 or about 4.0 inches, or about 5.0 inches or more. The layer 12 has a thickness of about 2 mm, or about 4 mm, or about 6 mm, to about 8 mm, or about 10 mm, or about 12 mm, or more. In a specific embodiment of the invention, layer 12 is made of a porous polyethylene and has thickness of about 0.38 inch (about 10 mm).

The absorbent layer 12 includes a substantially centrally located through aperture 18 having a size and shape suitable for exposing the intended area of a body to be treated when the apparatus is placed on the body with the perimeter of the through aperture 18 substantially circumscribing the intended area.

The second layer 14 preferably is structured of a material that does not readily absorb a skin preparation agent, for example an evaporative coolant, for example a vapocoolant, to be applied to the intended area. For example, the second layer 14 may comprise a substantially solid, or substantially non-porous material, for example, a material that is relatively harder and/or more rigid than the material from which the first layer 12 is made.

In a preferred embodiment of the invention, second layer 14 is made of a polymeric material, for example, a polyolefin material, for example, a polyethylene material.

Although the second layer 14 is harder and/or more rigid than the first layer 12, it should be understood that the entire member 10, and therefore layers 12 and 14, are preferably sufficiently flexible to allow the layer 12 to closely conform to the desired area of a human body, for example, an irregularly shaped area of a human body as described elsewhere herein. The second layer 14 is preferably structured to be effective to provide increased pressure and/or force to the layer 12, for example, through manual application of pressure and/or force on second layer 14, so as to effectively allow member 10, and in particular layer 12, to closely and tightly conform to the desired area of the human body.

Member 10 can be made using one or more conventional composite manufacturing techniques. Those of ordinary skill in the art will be able to produce the present apparatus based on the disclosure set forth herein. By way of example, first and second layers 12, 14 can be individually or independently produced, using conventional techniques, and thereafter secured together using conventional means. Layers 12, 14 may be bonded together using conventional heat bonding techniques. Preferably, no adhesives are used in the bonding process. The layers 12, 14 may be bonded using conventional ultrasound processing. For example, an ultrasound horn may be applied to the first or second layer and ultrasound may be radiated into the layers to cause bonding between the layers 12, 14, for example at or near the outer periphery of the second layer 14.

Figure 3:
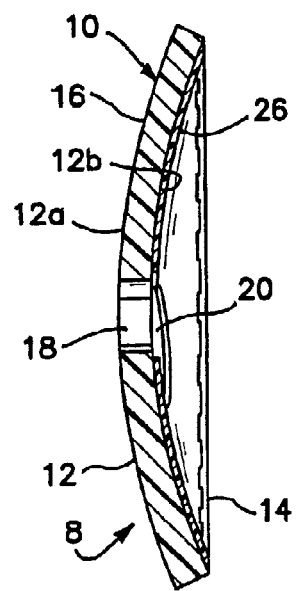
FIG. 3 is a cross-sectional view of the shield member taken along a vertical line through the center of FIG. 2.

In any event, second surface 12b of first layer 12 is in an abutting relation to second layer 14, as best shown in FIG. 3.

Figure 2:
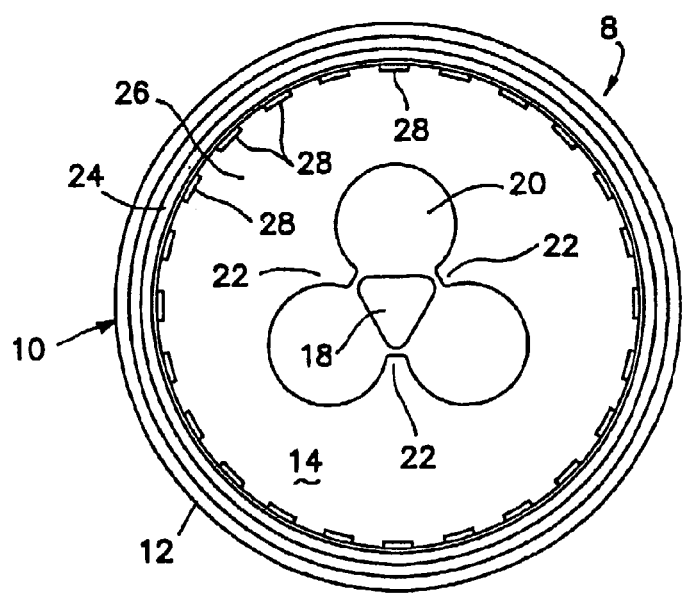
FIG. 2 is a front plan view of the shield member shown in FIG. 1.

As shown, the second layer 14 includes a second through aperture 20 that overlaps, for example encompasses, first through aperture 18. As shown in FIGS. 1 to 3, the second through aperture 20 is larger in size than the first through aperture 18. In some embodiments, the second through aperture has a cross-section of at least about 2 times or at least about 3 times the cross sectional area of the first through aperture. In other embodiments, second through aperture 20 has a cross sectional area that is about 25% larger, or about 50% larger, or about twice as large as the first through aperture 18. In this particular embodiment, second through aperture 20 is shown as having a tri-lobe configuration. Although not essential to the effectiveness of the present invention, this tri-lobe configuration facilitates ease of use and effectiveness of the member 10, as will be described elsewhere herein.

Preferably, the second through aperture 20 is configured to enhance contact between the body surface and the first layer. For example, the second through aperture 20 has a configuration, for example, a shape and/or size and/or thickness, that facilitates applying increased force or pressure on the first layer to cause the first layer to conform to one or more irregularly shaped areas of the human body, for example, relative to a reference second through aperture defining a circular shape (having a circular cross-section) and having the same cross-sectional area as the second through aperture 20.

For example, in a preferred embodiment of the invention, second through aperture 20 is defined in part by at least one, and more preferably a plurality of inwardly extending fingers or projections 22. Such projections 22 extend inwardly toward the first through aperture 18. The projections 22 enhance pressure or force on portions of the first layer 12 immediately surrounding the first through aperture 18 when the member 10 is located on a body area and manual pressure is being applied to the second layer 14. The enhanced pressure causes the first layer 12 to more closely conform to the contours of the area of the human or animal body around or in proximity to the exposed body area to be treated, relative to an otherwise identical member without the projections 22.

The advantages of the present invention may be more clearly understood and appreciated with reference to the following non-limiting example. Member 10 is placed in contact with a human body with the first through aperture 18 substantially circumscribing an intended area to be injected with a therapeutically or cosmetically beneficial material. To prepare the skin and mitigate against pain experienced by the patient, a skin preparation agent, for example an anesthetizing agent, preferably an evaporative coolant, is applied to the intended area by spraying the coolant at or toward the aperture 18 while the physician presses against the second layer 14 to cause close contact between the first layer 12 and the patient's skin. The portion of the absorbent layer 12 exposed through second aperture 20 absorbs or catches that portion of skin preparation agent spray that misses or does not pass through the first aperture 18. In this manner, only the body area circumscribed by the first aperture 18 is exposed to and prepared, for example anesthetized, for example cooled, by the evaporative coolant. Absorbing the excess agent in layer 12 also is effective to reduce spillage of agent, for example condensed coolant.

An additional feature of shield member 10 which is effective to reduce spillage of excess skin preparation agent, for example condensed coolant, is an upwardly extending peripheral rim 24 which catches or holds condensed coolant on the outer surface 26 of relatively non-absorbent second layer 14. A still further feature to reduce spillage includes peripheral openings 28 in second layer 14, located inwardly of rim 24. Such openings 28 expose portions of absorbent layer 12, so that condensed coolant held by rim 24 is absorbed in those portions of absorbent layer 12.

Member 10 is preferably configured so that, when the member 10 is at rest, it assumes a somewhat dome-shaped configuration. More specifically, in the embodiment shown, the outer surface 26 of second layer 14 is substantially concave and the outer surface 16 of first layer 12 is substantially convex. This configuration is effective in facilitating closely conforming contact between the first layer 12 and the body, even an irregularly shaped region of the body, when manual pressure is applied against the second member 14. Member 10 is sized and shaped to be comfortably and easily held and manipulated by a single adult human hand.

In methods of the invention that utilize an evaporative coolant as a skin preparation material, the evaporative coolant may be chosen from any evaporative coolant suitable for providing the desired amount of cooling to the body area in question. Although the evaporative coolant may be ethyl chloride and the like materials, in one very useful embodiment, the evaporative coolant includes one or more other halogen-containing organic compounds such as fluoro carbons, chloro hydrocarbons, mixtures of the same and the like. In particular, although the fluoro carbons and/or chloro carbons do not provide the amount of cooling (on a weight basis) obtainable using ethyl chloride, the amount of cooling provided by such materials is sufficient to achieve the results desired in accordance with the present invention. A very useful evaporative coolant for use in the present invention is an HFC-based coolant recently FDA-approved for pre-injection anesthesia. One such coolant is sold by Gebauer Company.

By confining the evaporative coolant to the intended area of the human body, the remainder of the human body is not exposed to the evaporative coolant and is not cooled by the evaporative coolant. Thus, only limited exposure to the evaporative coolant is obtained.

In one possible use, shield member 10 is placed in contact with a human body so that the area of the body to be injected is circumscribed by the first through aperture 18. An evaporative coolant is sprayed toward aperture 18, thereby cooling the circumscribed area of the body. The shield member 10 is removed, or remains in place, and the injection or injections are substantially immediately administered. The patient experiences less pain/anxiety and an increased level of comfort during and after the injection/injections.

Figure 4:
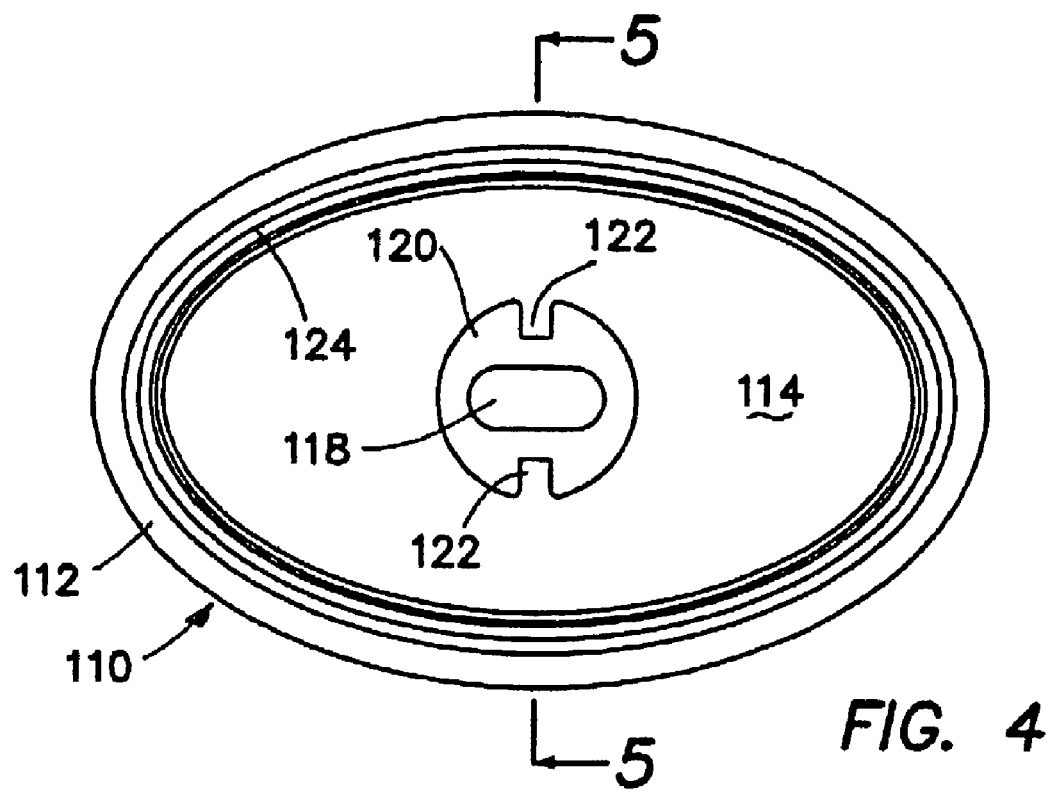
FIG. 4 is a perspective view of an alternate embodiment of a coolant spray shield member in accordance with the present invention roughly shown in a shape created by the user's hand as the shield is squeezed and bent together to cause the device to be better shaped to conform to a more concave area of the body.
Figure 5:
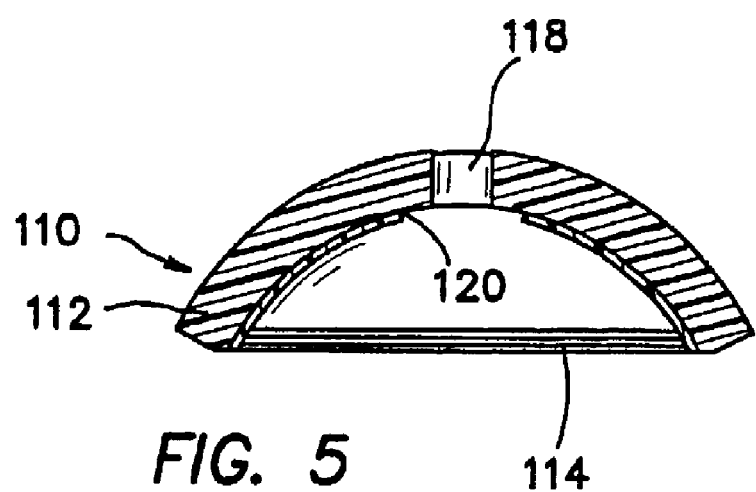
FIG. 5 is a cross-sectional view of the shield member taken above line 5-5 of FIG. 4.

FIGS. 4 and 5 illustrate an alternate shield member, shown generally at 110, in accordance with the present invention. Except as expressly stated herein, shield member 110 is structured and functions similarly to shield member 10. Components of shield member 110 which correspond to components of shield member 10 are indicated by the same reference numeral increased by 100.

One primary difference between shield member 110 and shield member 10 relates to the configurations, for example shapes, of first through aperture 118 and second through aperture 120. First through aperture 118 is relatively narrow and elongated, for example is substantially linear, relative to first aperture 18. The shape of first aperture 118 reflects that the use of shield member 110 is to isolate a different area of the body, for example, an elongated or linear area, relative to shield member 10. In general, the size and/or shape of the first through aperture of the present apparatus may be, and preferably is, varied to fit the application for which the apparatus is to be used.

In addition, the size and shape of the second through aperture 120 has been varied relative to second through aperture 20. In effect, the size and shape of second through aperture 120 has been modified to accommodate the size and shape of the first through aperture 118. It should be noted that the size and shape of the first and second through apertures, as well as the size and shape of the present shield member itself, may be varied to suit the particular application involved or to be addressed.

Note that inwardly extending projections or fingers 122 are present, as well as peripheral rim 124 is present. Shield member 110 as shown does not include any peripheral openings, such as peripheral openings 28 shown in FIG. 1.

In another aspect of the invention, methods are provided for preparing a human or animal body for localized treatment, for example, for injection. Such methods generally comprise the steps of providing an apparatus, preferably apparatus of the present invention comprising a member as described elsewhere herein, and placing the member in contact with a human or animal body so that the first layer is in contact with the body and the first through aperture substantially circumscribes an intended area of the body to be treated. The method further comprises preparing the intended area for treatment by passing a skin preparation agent, for example an evaporative coolant, through the first and second through apertures while the member is so placed. The intended are is then treated as desired.

Methods of the invention are also provided for treating a localized area of a human or animal body. These methods generally include the steps of preparing the area, for example as described hereinabove, and treating the area with or without the member of the invention in place on the body.

While this invention has been described with respect to various specific examples and embodiments, it is to be understood that the invention is not limited thereto and that it can be variously practiced within the scope of the following claims.

What is claimed is:

1. An apparatus for isolating an area of a human or animal body for localized cooling comprising:
 a member comprising
  a first layer including an absorbent first material and having a first surface, a substantially opposing second surface and a first through aperture extending between the first and second surfaces, the first through aperture being sized to allow an evaporative coolant to pass therethrough and come into contact with an area of a human or animal body when the first surface of the first layer is placed in proximity to the area of the human or animal body; and
  a second layer including a second material, a second through aperture overlapping the first through aperture and one or more fingers extending into the second through aperture, the second layer being secured to the first layer and located in proximity to the second surface of the first layer, wherein the member is configured so that the first surface of the first layer is convex when the member is at rest.

2. The apparatus of claim 1 wherein the second through aperture substantially encompasses the first through aperture.

3. The apparatus of claim 1 wherein the second material is relatively less absorbent than the first material.

4. The apparatus of claim 1 wherein the first material is a porous polymeric material.

5. The apparatus of claim 1 wherein the member is sufficiently flexible to conform to one or more irregularly shaped areas of a human or animal body.

6. The apparatus of claim 1 wherein the second through aperture has a configuration that facilitates applying increased pressure on the first layer to cause the first layer to conform to one or more irregularly shaped areas of a human or animal body.

7. The apparatus of claim 1 wherein the first layer is heat bonded to the second layer.

8. The apparatus of claim 1 wherein the second layer includes structure effective to capture condensed evaporative coolant.

9. The apparatus of claim 8 wherein the structure comprises at least one of a plurality of ribs and a plurality of openings adjacent a periphery of the second layer.

10. An apparatus for isolating an area of a human or animal body for localized cooling comprising:
 a member comprising
  a first layer including an absorbent first material and having a first surface, a substantially opposing second surface and a first through aperture extending between the first and second surfaces, the first through aperture being sized to allow an evaporative coolant to pass therethrough and come into contact with an area of a human or animal body when the first surface of the first layer is placed in proximity to the area of the human or animal body; and
  a second layer including a second material and a second through aperture overlapping the first through aperture, the second layer being secured to the first layer and located in proximity to the second surface of the first layer, wherein the second layer includes one or more fingers extending into the second through aperture.

11. The apparatus of claim 10 wherein the second through aperture substantially encompasses the first through aperture.

12. The apparatus of claim 10 wherein the second material is relatively less absorbent than the first material.

13. The apparatus of claim 10 wherein the member is sufficiently flexible to conform to one or more irregularly shaped areas of a human or animal body.

14. The apparatus of claim 10 wherein the second through aperture has a configuration that facilitates applying increased pressure on the first layer to cause the first layer to conform to one or more irregularly shaped areas of a human or animal body.

15. An apparatus for isolating an area of a human or animal body for localized cooling comprising:
 a member comprising
  a first layer including an absorbent first material and having a first surface, a substantially opposing second surface and a first through aperture extending between the first and second surfaces, the first through aperture being sized to allow an evaporative coolant to pass therethrough and come into contact with an area of a human or animal body when the first surface of the first layer is placed in proximity to the area of the human or animal body; and
  a second layer including a second material and a second through aperture overlapping the first through aperture, the second layer being secured to the first layer and located in proximity to the second surface of the first layer, wherein the second layer includes a structure effective to capture condensed evaporative coolant, and the structure comprises at least one of a plurality of ribs and a plurality of openings adjacent a periphery of the second layer.

16. The apparatus of claim 15 wherein the second through aperture substantially encompasses the first through aperture.

17. The apparatus of claim 15 wherein the second material is relatively less absorbent than the first material.

18. The apparatus of claim 15 wherein the member is sufficiently flexible to conform to one or more irregularly shaped areas of a human or animal body.

19. The apparatus of claim 15 wherein the second through aperture has a configuration that facilitates applying increased pressure on the first layer to cause the first layer to conform to one or more irregularly shaped areas of a human or animal body.

* * * * *